United States Patent [19]

Jew et al.

[11] Patent Number: 6,013,666

[45] Date of Patent: Jan. 11, 2000

[54] OXIRANE CARBOXYLIC ACID DERIVATIVE AND ITS MANUFACTURING METHOD

[75] Inventors: Sang Sup Jew, 6-404, Seorak Apt., Jamwon-dong, Seocho-gu; Suk Ku Kang; Deuk Joon Kim, all of Seoul; Won Ki Kim; Hwa Jung Kim, both of Kyunggi-do; Chang Kiu Moon; Jeong Hill Park, both of Seoul; Young Ger Suh, Kyunggi-do; Bong Jin Lee, Seoul; Jee Woo Lee, Seoul; Ki Hwa Jung, Seoul; Moon Woo Chun, Seoul; Hoon Huh, Seoul; Eung Seok Lee, Seoul; Hyung Ook Kim, Seoul; Eun Kyung Kim, Daegu; Sung Jin Kim, Seoul; Jae Hoon Cheong, Kyunggi-do; Kwang Ho Ko; Bak Kwang Kim, 449-39, Sadang 1-dong, Dangjak-gu, both of Seoul, all of Rep. of Korea

[73] Assignees: Sang Sup Jew; Kang Ho Kang; Bak Kwang Kim, all of Seoul, Rep. of Korea

[21] Appl. No.: 09/214,389

[22] PCT Filed: Jul. 2, 1997

[86] PCT No.: PCT/KR97/00132

§ 371 Date: May 11, 1999

§ 102(e) Date: May 11, 1999

[87] PCT Pub. No.: WO98/00422

PCT Pub. Date: Jan. 8, 1998

[30] Foreign Application Priority Data

Jul. 2, 1996 [KR] Rep. of Korea ...................... 96/26775
Jul. 2, 1996 [KR] Rep. of Korea ...................... 96/26776

[51] Int. Cl.$^7$ ..................... A61K 31/335; A61K 31/38; C07D 307/02; C07D 241/02; C07D 401/00

[52] U.S. Cl. ..................... 514/475; 514/255; 514/336; 514/406; 514/407; 514/444; 514/461; 514/471; 514/472; 514/473; 549/549; 549/518; 549/60; 549/472; 549/473; 544/406; 544/407; 544/409; 546/281.7; 548/365.7

[58] Field of Search ..................... 549/549, 518, 549/60, 472, 473; 514/475, 471, 472, 473, 461, 444, 255, 336, 406, 407; 544/406, 407, 409; 546/281.7; 548/365.7

[56] References Cited

U.S. PATENT DOCUMENTS

| 3,810,931 | 5/1974 | Guthrie et al. | 549/549 |
|---|---|---|---|
| 3,970,758 | 7/1976 | Pallos et al. | 549/60 |
| 4,933,365 | 6/1990 | Marshall et al. | 514/475 |
| 4,946,866 | 8/1990 | Wolf et al. | 415/475 |
| 5,132,435 | 7/1992 | Bousquet et al. | 549/60 |
| 5,190,969 | 3/1993 | Blumenstein et al. | 514/422 |
| 5,679,708 | 10/1997 | Tsubotani et al. | 514/475 |
| 5,710,148 | 1/1998 | Sudo et al. | 514/475 |
| 5,843,992 | 12/1998 | Nomura et al. | 514/475 |

FOREIGN PATENT DOCUMENTS

WO 93/18036 9/1993 WIPO.

OTHER PUBLICATIONS

Romo de Vivar et al, "Eupaglabrin, a terpene from Eupatorium glabratum", CA75:45625, 1971.

"A new general method to obtain chiral 1–alkylglycidic acid derivatives: synthesis of methyl (R)–(+)–palmoxirate", Chem. abstr., vol. 120, No. 19, May 9, 1994, p. 982, abstr. No. 244463r, Garcia Ruano J.L. et al.

"Asymmetrization of 2–substituted glycerols: syntheses of R–etomoxir and R–palmoxirate", Chem. abstr., vol. 114, No. 9, Mar. 4, 1991, p. 697, abstr. No. 81443u, Prasad, K. et al.

*Primary Examiner*—Deborah C. Lambkin
*Attorney, Agent, or Firm*—Finnegan, Henderson, Farabow, Garrett & Dunner, L.L.P.

[57] ABSTRACT

This invention relates to a novel oxirane carboxylic acid derivative and thereof manufacturing method. Based on thereof mechanism to inhibit the CPT I, oxirane carboxylic acid derivative of this invention has blood glucose lowering effects so that the derivative may be effectively used as an antidiabetic agent having remarkable antidiabetic activity and less side effects.

10 Claims, No Drawings

OXIRANE CARBOXYLIC ACID DERIVATIVE AND ITS MANUFACTURING METHOD

TECHNICAL FIELD

This invention relates to oxirane carboxylic acid derivative expressed by the following formula (1), its manufacturing method and antidiabetic agent containing it.

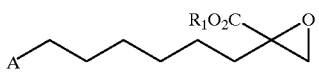

Wherein

A is one selected from the radicals expressed by the following (i), (ii), (iii) and (iv);

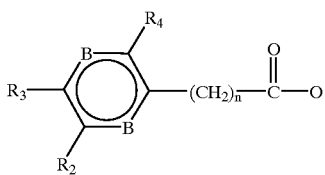

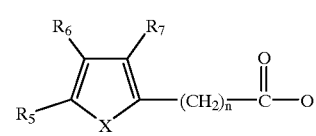

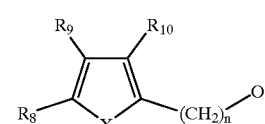

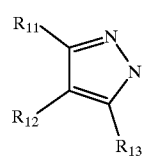

$R^1$ represents a lower alkyl;

(wherein, $R_2$~$R_{13}$ represent independently hydrogen, halogen, alkoxy, lower alkyl, hydroxy, alkenyl, alkynyl, cyano or amino group; B is independently nitrogen or carbon; X is oxygen or sulfur; n denotes 0, 1 or 2).

BACKGROUND OF ART

The diabetic patients tend to suffer from some disorders such as inhibition of glucose uptake, inhibited glycolysis and increasing beta-oxidation of fatty acid in their peripheral tissues, which cause the use of fat for their body's energy source instead of glucose and lead to some diseases such as hyperglycemia, hyperlipidemia and hyperketonemia.

The beta-oxidation of fat in diabetic patients occurs in a mitochondrial substrate. Carnitine palmitoyl transferase I (CPT I) is an enzyme to transport a higher fatty acid from cytoplasm to a mitochondrial substrate, and plays an vital role in limiting the beta-oxidation rate.

Therefore, CPT I inhibitors will be utilized as an effective antidiabetic agent in that they may inhibit the beta-oxidation of higher fatty acids, increase the availability of glucose and exert the hypoglycemic, hypolipidemic and hypoketonemic effects.

The typical compounds belonging to the above mentioned CPT I inhibitors include palmoxirate, clomoxir(POCA) and etomoxir, and these compounds are characterized in that all of them have oxirane carboxylic acid in their most active site.

The inhibitory action of these oxirane carboxylic acid derivatives against the CPT I has yet to be elucidated up to now but it has been assumed that since these derivatives have the stable covalent bonding in the active sites of CPT I within cytoplasm, their inhibition action against the CPT I may contributed to the treatment of diabetes. Therefore, a possible mode of action is that when some nucleophilic substance at the active site of CPT I initiates to attack the epoxide ring structure of oxirane carboxylic acid derivatives, the opened epoxide ring forms a new hydroxyl group, and at the same time CPT I and oxirane carboxylic acid derivative is covalently bonded, thus the CPT I activity is inhibited.

However, the phase II clinical trials of etomoxir had not been continued owing to some side effects associated with prolonged administration, such as enlarged heart and toxicity in the liver, but its cause has not been explicitly known up to now.

DISCLOSURE OF INVENTION

Based on the mechanism that these oxirane carboxylic acid derivatives have exerted inhibitory actions against the CPT I, the inventor et al. have extensively studied to develop some promising compounds with blood glucose lowering effects, thus showing remarkable antidiabetic activities and less side effects. To this end, the inventor et al. have come to know that as a result of screening various kinds of derivatives having oxirane carboxylic acid positioned at their most active sites, oxirane carboxylic acid derivative of the formula 1 with opened epoxy ring at oxirane structure has proven to have an excellent antidiabetic activity and less side effects. In consequence, this invention has been completed.

An object of this invention is to provide oxirane carboxylic acid derivative expressed by the following formula 1.

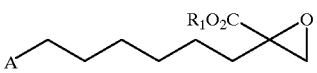

Wherein:

A is one selected from the radicals expressed by the following (i), (ii), (iii), (iv) and (v);

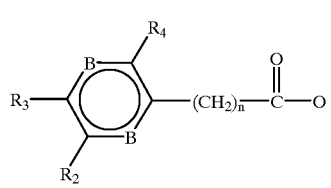

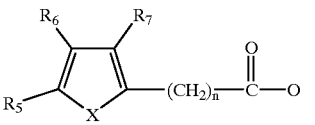

3

-continued (iii)
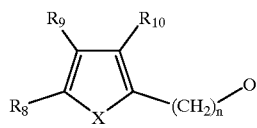

(iv)
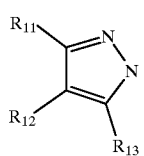

$R_1$ represents a lower alkyl;

4

(wherein, $R_2 \sim R_{13}$ represent independently hydrogen, halogen, alkoxy, lower alkyl, hydroxy, alkenyl, alkynyl, cyano or amino group; in particular, $R_2$ is hydrogen, bromine or chlorine; $R_3$ is hydrogen, methyl, n-buthyl, chlorine or methoxy; $R_4$ is hydrogen or methoxy; $R_5$ is hydrogen or bromine; $R_6$, $R_7$, $R_9$, $R_{12}$ are hydrogen; $R_8$ is hydrogen, methyl, chlorine or methoxy; $R_{10}$ is hydrogen or chlorine; $R_{11}$, $R_{13}$ are preferably methyl; B is independently nitrogen or carbon; X is oxygen or sulfur; n denotes 0, 1 or 2).

Another object of this invention is to provide some compounds expressed by the above mentioned formula 1.

Another object of this invention is also to provide an antidiabetic agent containing some compounds expressed by the above mentioned formula 1.

The compound of the formula 1 according to this invention may be prepared by the following reaction scheme 1:

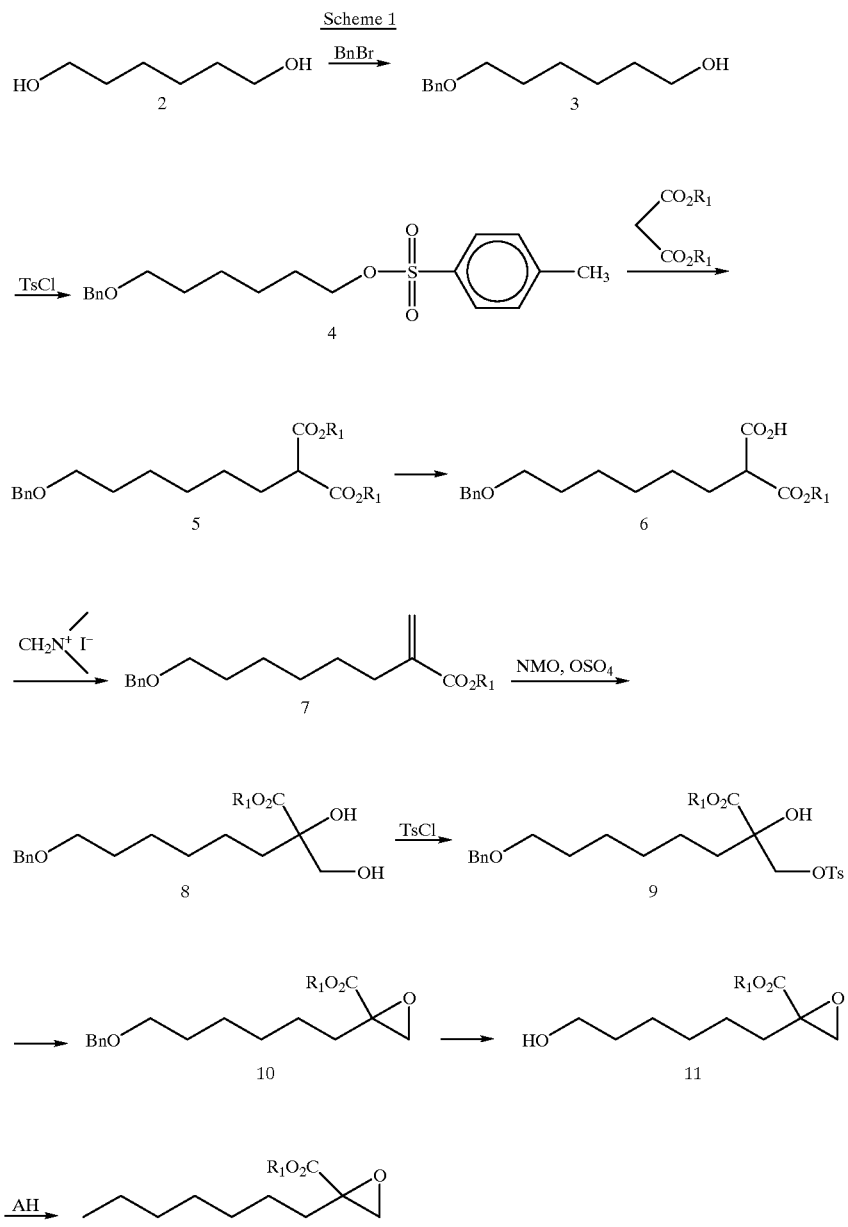

(wherein: A and $R_1$ are the same as defined above.)

The aforementioned reaction scheme is explained as follows:

a) 1,6-hexanediol of the structural formula 2, a well known substance and starting material, is treated with sodium hydride as a base to synthesize 6-benzyloxy-1-hexanol of the structural formula 3 with substituted benzyl ring;

b) The compound of the formula 3 is tosylated to furnish the compound of the structural formula 4;

c) The compound of the structural formula 4 is reacted with dimalonate to synthesize dialkyl-6-benzoxyhexylmalonate of the general formula 5;

d) The compound of the general formula 5 is hydrolyzed using potassium hydride to furnish the compound of the general formula 6;

e) Eschernmorser's salt is added to the compound of the general formula 6 to synthesize the alpha, beta-unsaturated ester of the general formula 7;

f) The compound of the general formula 7 is catalyzed by osmium tetroxide to give the compound of the general formula 8;

g) The compound of the general formula 8 is further tosylated to synthesize alkyl-2-hydroxy-3-(4-methylbenzenesulfoxy)-2-(6-benzoxy)hexylpropionic acid of the general formula 9;

h) The compound of the general formula 9 is treated with potassium carbonate as a base to give alkyl-2-(6-benzoxy)hexyloxirane-2-carboxylic acid of the general formula 10, followed by the intermolecular cyclic reaction;

i) The compound of the general formula 10 is hydrogenated to give the compound of the general formula 11 with its benzyl group deprotected;

j) The compound of the general formula 11 is treated with DCC, DMAP and methane dichloride to give oxirane carboxylic acid derivative of the formula 1, a desired compound, via esterification, etherification or amidofication with AH of the general formula.

Meantime, in case where A, a substituent of the final reaction process, is a radical (i) or (ii), the ester linkage of a final product is relatively strong in its reactability and to increase the yield, it is preferred to perform the substitution after intermolecular cyclization. However, if the above A is a radical (iii) or (iv), a final product having an ether or amide linkage is relatively stabilized, it is possible to perform the substitution prior to intermolecular cyclization. The above matter is explained in more detail as illustrated in the following reaction scheme 2.

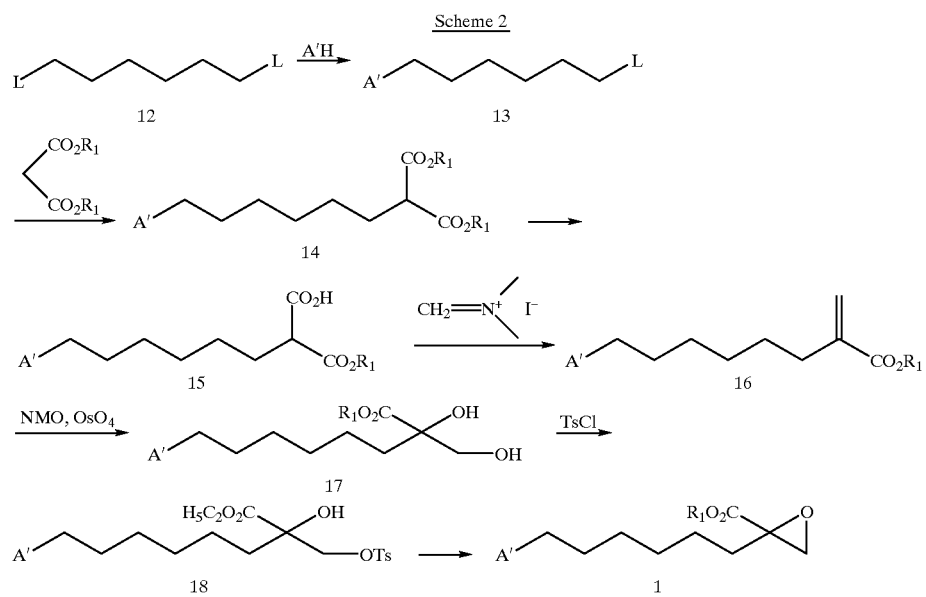

Scheme 2

(wherein, A' is a radical (iii) or (iv) as defined above; $R_1$ is the same as defined above; L is bromine or mesylate).

From the above reaction scheme 2, the first step is a reaction in which radical A' is substituted; the structural 12, a starting material, is reacted with A'H in the presence of sodium hydride and base to obtain the compound 13. The compound 12 is used as a starting material where the leaving group is attached to its terminal group so as to facilitate the substitution; if the leaving group is mesylate, the compound 12 may be obtained by the reaction of 1,6-hexanediol with methanesulfonyl chloride.

As illustrated in the reaction scheme 1, the compound 13, so formed, is reacted with dimalonate and followed by the intramolecular cyclization, oxirane carboxylic acid derivative of the formula 1 may be obtained as a final product.

The compound of the formula 1 according to this invention may be used as an effective antidiabetic agent. The daily effective dose in adult is 10–100 mg/kg.

The compound of the formula I according to this invention has proven to have remarkable blood glucose lowering effects, while being safe in $LD_{50}$.

According to this invention, an antidiabetic agent containing the compound of the formula 1 as an active ingredient may be administered via the following common dosage forms, i.e., tablets, injections, capsules, etc.

This invention relates to a novel oxirane carboxylic acid derivative and its manufacturing method. Based on its inhibitory mechanism on the CPT I, oxirane carboxylic acid derivative of this invention has blood glucose lowering effects so that the above derivative may be effectively used as an antidiabetic agent having remarkable antidiabetic activity and less side effects.

BEST MODE FOR CARRYING OUT THE INVENTION

This invention is explained in more detail by the following examples, but the claims are not limited to these examples.

EXAMPLE 1

Ethyl-2-[6-(4-chlorophenylcarboxyl)hexyl]-oxirane-2-carboxylic acid

1) In a 500 ml round-bottomed flask, 60% sodium hydride (6.84 g, 170.92 mmol) was placed, and the air inside the flask was substituted by argon gas. Dry tetrahydrofuran (200 ml) was added dropwise thereto to form a suspension. After cooling the mixture to 0° C., a solution of 1,6-hexanediol (20 g, 169.23 mmol) in dry tetrahydrofuran (200 ml) was slowly added dropwise, and the mixture stirred at room temperature for 20 minutes. Benzyl bromide (20.25 ml, 170.25 mmol) was added dropwise thereto stirred at room temperature for 18 hrs and the reaction mixture was concentrated under reduced pressure to remove tetrahydrofuran as a solvent. The residue was diluted with a mixture of ethyl acetate (400 ml) and water (50 ml). After washing with water (500 ml×2) and saturated brine (500 ml×2), the solution was dried over anhydrous magnesium sulfate, filtered and concentrated under reduced pressure. The residue was purified on a column chromatography (eluent:ethyl acetate/n-hexane=1/3) to give 19.47 g of object compound as colorless oil (yield: 55%).

IR(neat) 3400(alcohol) cm$^{-1}$

Mass(EI) 208(M$^+$−1)

$^1$H-NMR (80 MHz, CDCl$_3$) δ 7.43(s, 5H), 4.53(s,2H), 3.66(t, 2H), 3.50(t, 2H), 1.81–1.20(m, 8H)

2) In a 250 ml round-bottomed flask, 6-benzyloxy-1-hexanol (14.2 g, 67.87 mmol) and p-toluenesulfonyl chloride (14.23 g, 74.66 mmol) were placed, and the air inside the flask was substituted by argon gas. Dry chloroform (120 ml) was added dropwise thereto, and then dry pyridine (16.47 ml) was injected to the mixture. After stirring at room temperature for 3 hours, the reaction mixture was concentrated under reduced pressure to remove chloroform, and the residue was diluted with ethyl acetate (400 ml). The solution was washed with diluted aqueous hydrochloric acid (20 ml×2), water (30 ml×2) and saturated brine (30 ml×2), dried over anhydrous magnesium sulfate and filtered. After concentrating the solution under reduced pressure, the residue was purified on a column chromatography (eluent:ethyl acetate/n-hexane=1/10) to obtain 24 g of the object compound as colorless oil (yield: 97%).

Mass(EI) 362(M$^+$−1)

$^1$H-NMR (400 MHz, CDCl$_3$) δ 7.63(d, 2H), 7.15(s, 7H), 4.33(s, 2H), 3.86(t, 2H), 3.27(t, 2H), 2.29(s, 3H), 1.52–1.11 (m, 8H)

3) Diethyl malonate (1.85 ml, 12.19 mmol, 1.1 eq.) was dissolved in dry tetrahydrofuran (25 ml), and the solution chilled to 0° C. Sodium hydroxide (95%) (308 mg, 12.19 mmol, 1.1 eq.) was added thereto, and the resultant mixture stirred about 10 minutes at the same temperature. To the mixture, a solution of 6-benzoxy-1-(4-methylbenzenesulfoxy)hexane (3.24 g, 11.08 mmol) in tetrahydrofuran (20 ml) was slowly added dropwise, and the mixture stirred for a while. After heating under reflux for 16 hours, the mixture was concentrated under reduced pressure to remove tetrahydrofuran. The residue was diluted with ethyl acetate (150 ml) and the solution washed with distilled water (120 ml), 1N aqueous hydrochloric acid (120 ml×2), 5% sodium bicarbonate (120 ml×2) and saturated brine (80 ml). Then the solution was dried over anhydrous magnesium sulfate, filtered, and concentrated under reduced pressure. The obtained residue was purified on a column chromatography (ethyl acetate/n-hexane=1/5) to give diethyl 6-benzoxyhexylmalonate (3.5 g, 88.6%) as pale yellow clear oil.

$^1$H-NMR (300 Hz, CDCl$_3$) δ 7.28(q, 1H), 7.0–6.95(m, 2H), 4.65(s, 2H), 4.2(q, 4H), 3.46(t, 2H), 3.3(t, 1H), 1.9(m, 2H), 1.6(m, 2H), 1.32(m, 6H), 1.27(t, 6H)

4) Diethyl 6-benzoxyhexylmalonate (3.5 g, 9.82 ml) was dissolved in absolute ethanol (30 ml), and potassium hydroxide (85%) (694 mg, 10.51 mmol, 1.07 eq.) was added thereto. After stirring about 4–5 hours at ambient temperature, the reaction mixture was concentrated under reduced pressure to remove ethanol. The residue was diluted with distilled water (150 ml), and the organic impurities were washed by using ethyl acetate. The water layer was acidified with 1N aqueous hydrochloric acid to pH 2–3, extracted with ethyl acetate (50 ml×3), and washed with 1N aqueous hydrochloric acid (100 ml) and saturated brine (80 ml). The extract was dried over anhydrous magnesium sulfate, filtered and concentrated under reduced pressure to give ethyl 6-benzoxyhexyl malonate (2.42 g, 75%) as pale yellow clear oil.

$^1$H-NMR (300 MHz, CDCl$_3$) δ 7.28(q, 1H), 7.0–6.95(m, 2H), 4.66(sd, 2H), 4.22(q, 2H), 3.46(t, 2H), 3.36(t, 1H), 1.9(m, 2H), 1.6(m, 2H), 1.34(m, 6H), 1.28(t, 3H)

5) Dissolved was ethyl 6-benzoxyhexylmalonate (2.42 g, 7.37 ml) in dry tetrahydrofuran (70 ml), and sodium hydride (335 mg, 13.27 mmol, 1.8 eq.) was added thereto at 0° C. The mixture was stirred at room temperature for 20 to 30 minutes. When sodium hydride was practically dissolved, Eschenmoser salt (1.64 g, 8.84 mmol, 1.2 eq.) was added in solid state. After stirring for a while, the mixture was heated under reflux for 16 hours. The reaction mixture was concentrated under reduced pressure to remove tetrahydrofuran, and the residue was diluted with ethyl acetate (150 ml), and washed with distilled water (120 ml), 1N aqueous hydrochloric acid (120 ml×2), 5% sodium bicarbonate (120 ml×2) and saturated brine (80 ml). The solution was dried over anhydrous magnesium sulfate, filtered and concentrated under reduced pressure. The residue was purified on a column chromatography (ethyl acetate/n-hexane=1/10) to obtain ethyl 2-(6-benzoxy)hexyl-2-enepropionate (1.82 g, 83%) as pale yellow clear oil.

$^1$H-NMR (300 MHz, CDCl$_3$) δ 7.28(q, 1H), 7.0–6.95(m, 2H), 6.12(d, 1H), 5.05(d, 1H), 4.65(sd, 2H), 4.20(q, 2H), 3.47(t, 2H), 2.29(m, 2H), 1.60(m, 2H), 1.45(m, 2H), 1.35(m, 4H), 1.30(t, 3H).

6) To a mixture of distilled water (32 ml), NMO (60 wt %)(1.17 ml, 6.75 mmol, 1.1 eq.) and acetone (28 ml), a solution of 2.5% osmium tetroxide in t-butanol (0.1 M) (3.07 mmol, 0.05 eq.) and t-butanol (10 ml) were added and the mixture stirred. The mixture was added to ethyl 2-(6-benzoxy)hexyl-2-enepropionate (1.82 g, 6.14 mmol), and the resultant mixture stirred at room temperature for 1.5 hours. To the mixture, $Na_2S_2O_4$ (about 2 g) was added to quench the reaction, and the reaction mixture was concentrated under reduced pressure to remove acetone. The residue was diluted with ethyl acetate (150 ml), and the solution washed with distilled water (120 ml×3) and saturated brine (80 ml), and then dried over anhydrous magnesium sulfate. The residue after filtering and concentrating the solution under reduced pressure was purified on a column chromatography (eluent: ethyl acetate/n-hexane=1/2) to quantitatively obtain ethyl 2,3-dihydroxy-2-6-benzoxy)hexylpropionate (2.02 g) as colorless clear oil.

$^1$H-NMR (300 MHz, $CDCl_3$) δ 7.28(q, 1H), 7.0–6.95(m, 2H), 4.65(s, 2H), 4.27(dq—dq, 2H), 3.78 (t, 1H), 3.58(dd, 1H), 3.55(s, 1H), 3.46(t, 2H), 2.19(dd, 1H), 1.7–1.5(m, 3H), 1.4–1.0(m, 5H, t, 3H)

7) Ethyl 2,3-dihydroxy-2-(6-benzoxy)hexylpropionate (2.02 g, 6.11 mmol) was properly dissolved in pyridine (30 ml), and p-toluenesulfonyl chloride (11.65 g, 61.1 mmol, 10 eq.) was added thereto. After stirring about 3 hours, the reaction mixture was diluted by adding ethyl acetate (150 ml). The solution was washed with 1N aqueous hydrochloric acid (120 ml×3), 5% sodium bicarbonate (120 ml×2), distilled water (120 ml) and saturated brine (80 ml), and then dried over anhydrous magnesium sulfate, filtered and concentrated under reduced pressure. The residue was purified on a column chromatography (eluent:ethyl acetate/n-hexane=1/5) to give ethyl 2-hydroxy-3-(4-methylbenzenesulfoxy)-2-[6-benzoxyhexyl]propionate (2.56 g, 86.5%) as white solid.

$^1$H-NMR (300 MHz, $CDCl_3$) δ 7.77(d, 2H), 7.34(d, 2H), 7.28(s, 1H), 6.97(s, br, 2H), 4.63(s, 2H), 4.22(m, 3H), 3.08(d, 1H), 3.43(t, 2H), 3.35(s, 1H), 2.45(s, 3H), 1.7–1.4 (m, 4H), 1.4–1.15(m, 5H, t, 3H), 1.1(m, 1H)

8) In a 50 ml round-bottomed flask, ethyl 2-hydroxy-3-(4-methylbenzenesulfoxy)2-[6-benzoxyhexyl]propionate (250 mg, 0.52 mmol) and anhydrous potassium carbonate (71.86 mg, 0.52 mmol) were placed, and absolute ethanol (10 ml) was injected thereto. The mixture was stirred at room temperature for 5 hours, and concentrated under reduced pressure. The residue was purified on a column chromatography (eluent:ethyl acetate/n-hexane=1/2) to obtain the object compound (160 mg) as colorless oil (yield: 98%).

Mass(EI) 306($M^+$)

IR 1740(ester carbonyl)

$^1$H-NMR (500 MHz, $CDCl_3$) δ 7.33(s, 5H), 4.48(s, 2H), 4.22–4.20(m, 2H), 3.44(t, 2H), 3.01(d, 1H), 2.75(d, 1H), 1.54–1.29(m, 10H), 1.26(t, 3H)

9) In a Parr bottle, ethyl 2-[6-benzoxyhexyl]-2-oxirane carboxylate (528 mg, 1.725 mmol) and catalytic amount of 10% Pd/C were placed, and absolute ethanol was injected thereto. The mixture was stirred at room temperature for 5 hours under 40–50 psi hydrogen stream. The reaction mixture was filtered under reduced pressure and concentrated under reduced pressure, and the residue purified on a column chromatography (eluent:ethyl acetate/n-hexane) to obtain 360 mg of object compound as colorless oil (yield: 96%).

Mass(EI) 218($M^+$+2)

IR 1740(ester carbonyl) 3400(alcohol)

$^1$H-NMR (500 MHz, $CDCl_3$) δ 4.23–4.20(m, 2H), 3.63(t, 2H), 3.01(d, 1H), 2.76(d, 1H), 1.58–1.36(m, 10H), 1.28(t, 3H)

10) In a 25 ml round-bottomed flask, ethyl-6-hydroxyhexyloxirane-2-carboxylic acid (173 mg, 0.80 mmol), 4-chlorobenzoylcarboxylic acid (137 mg, 0.88 mmol), dicyclohexylcarbodiimide (181.57 mg, 0.88 mmol) and dimethylaminopyridine (9.77 mg, 0.80 mmol) were placed, and the air inside the flask was substituted by argon gas. After injecting dry methylene chloride (5 ml) thereto, the mixture was stirred at room temperature for 2 hours. The reaction mixture was filtered under reduced pressure and concentrated under reduced pressure, and the residue purified on a column chromatography (eluent:ethyl acetate/n-hexane=1/10) to obtain 280 mg of the object compound as colorless oil (yield: 98%).

MASS(EI) 354($M^+$)

IR 1740(ester carbonyl)

$^1$H-NMR(500 MHz, $CDCl_3$) δ 7.79(d, 2H), 7.41(d, 2H), 4.30(t, 2H), 4.23–4.18(m, 2H), 3.02(d, 1H), 2.78(d, 1H), 1.77–1.29(m, 10H), 1.28(t, 3H)

EXAMPLE 2

Ethyl-2-[6-(5-methyl-2-pyrazincarboxyl)hexyl]-oxirane-2-carboxylic acid

The procedures described in Example 1-1)~1-10) were repeated but using 5-methyl-2-pyrazincarboxylic acid instead of 4-chlorobenzoylcarboxylic acid of Example 1-10) to obtain the title compound.

IR(neat) 1740(ester carbonyl)

MASS(EI) 337($M^+$+1)

$^1$H NMR(500 MHz, $CDCl_3$) δ 9.16(d, 1H), 8.57(d, 1H), 4.42(t, 2H), 4.22–4.20(m, 2H), 3.01(d, 1H), 2.75(d, 1H), 2.66(s, 3H), 1.83–1.33(m, 10H), 1.28(t, 3H)

EXAMPLE 3

Ethyl-2-[6-(5-bromo-3-pyridincarboxyl)hexyl]-oxirane-2-carboxylic acid

The procedures described in Example 1-1)~1-10) were repeated but using 5-bromo-3-pyridincarboxylic acid instead of 4-chlorobenzoylcarboxylic acid of Example 1-10) to obtain the title compound.

IR(neat) 1740(ester carbonyl)

MASS(EI) 400($M^+$)

$^1$H-NMR(500 MHZ, $CDCl_3$) δ 9.11(s, 1H), 8.83(s, 1H), 8.41(s, 1H), 4.35(t, 2H), 4.23–4.20(m, 2H), 3.02(d, 1H), 2.76(d, 1H, 1.79–1.41(m, 10H), 1.28(t, 3H)

EXAMPLE 4

Ethyl-2-[6-(2,6-dimethoxy-5-pyridincarboxyl) hexyl]-oxirane-2-carboxylic acid

The procedures described in Example 1-1)~1-10) were repeated but using 2,6-dimethoxy-5-pyridincarboxylic acid instead of 4-chlorobenzoyl carboxylic acid of Example 1-10) to obtain the title compound.

IR(neat) 1740(ester carbonyl)

MAS(EI) 381($M^+$)

$^1$H NMR(500 MHz, $CDCl_3$) δ 8.11(d, 1H), 6.31(d, 1H), 4.24(t, 2H), 4.23–4.21(m, 2H),4.03(s, 3H), 3.96(s, 3H), 3.01(d, 1H), 2.76(d, 1H), 1.74–1.39(m, 10H), 1.28(t, 3H)

EXAMPLE 5

Ethyl-2-[6-(2-thiophenecarboxyl)hexyl]-oxirane-2-carboxylic acid

The procedures described in Example 1-1)~1-10) were repeated but using 2-thiophenecarboxylic acid instead of 4-chlorobenzoylcarboxylic acid of Example 1-10) to obtain the title compound.

IR(neat) 1740(ester carbonyl)

MASS(EI) 326(M$^+$)

$^1$H NMR(500 MHz, CDCl$_3$) δ 7.79(d, 1H), 7.54(d, 1H), 7.12–7.08(M, 1H), 4.28(t, 2H), 4.23–4.19(M, 2H), 3.01(d, 1H), 2.76(d, 1H), 1.76–1.40(m, 10H), 1.28(t, 3H)

$^{13}$C NMR (75 MHz, CDCl$_3$) δ 170.35, 162.26, 134.0, 133.21, 132.15, 127.66, 65.07, 61.54, 56.93, 51.79, 31.11, 29.08, 28.50, 25.71, 24.63, 14.08

EXAMPLE 6

Ethyl-2-[6-(2-pyrazincarboxyl)hexyl]-oxirane-2-carboxylic acid

The procedures described in Example 1-1)~1-10) were repeated but using 2-pyrazincarboxylic acid instead of 4-chlorobenzoylcarboxylic acid of Example 1-10) to obtain the title compound.

IR(neat) 1740(ester carbonyl)

MASS(EI) 322(M$^+$)

$^1$H-NMR(500 MHz, CDCl$_3$) δ 9.30(s, 1H), 8.78(d, 1H), 8.75(d, 1H), 4.44(t, 2H), 4.22–4.21(m, 2H), 3.01(d, 1H), 2.76(d, 1H), 1.84–1.41(m, 10H), 1.28(t, 3H)

EXAMPLE 7

Ethyl-2-[6-(2-thiopheneacetyl)hexyl]-oxirane-2-carboxylic acid

The procedures described in Example 1-1)~1-10) were repeated but using 2-thiopheneacetylic acid instead of 4-chlorobenzoylcarboxylic acid of Example 1-10) to obtain the title compound.

$^1$H NMR (300 MHz, CDCl$_3$) δ 7.22 (1H, dd, J=4.81 Hz, J=1.44 Hz, thiophene H$_5$), 6.96 (2H, m, thiophene H$_3$, H$_4$), 4.22 (2H, m, CO$_2$CH$_2$CH$_3$), 4.11 (2H, t, J=6.63 Hz, CO$_2$CH$_2$—), 3.83 (2H, s, Ar—CH$_2$CO$_2$—), 3.03 (1H, d, J=5.88 Hz, 1H of oxirane), 2.77 (1H, d, J=5.91 Hz, 1H of oxirane), 2.08 (1H, m, aliphatic H), 1.64 (3H, m, aliphatic H), 1.45~1.35 (6H, m, aliphatic H), 1.29 (3H, t, J=7.12 Hz, CO$_2$CH$_2$CH$_3$)

$^{13}$C NMR (75 MHz, CDCl$_3$) δ 170.48, 170.36, 135.17, 126.72 (2 C's), 124.96, 65.14, 61.54, 56.93, 51.79, 35.50, 31.09, 29.02, 28.33, 25.59, 24.59, 14.08

EXAMPLE 8

Ethyl-2-[6-(3-thiophenecarboxyl)hexyl]-oxirane-2-carboxylic acid

The procedures described in Example 1-1)~1-10) were repeated but using 3-thiophenecarboxylic acid instead of 4-chlorobenzoylcarboxylic acid of Example 1-10) to obtain the title compound.

$^1$H NMR (300 MHz, CDCl$_3$) δ 8.10 (1H, dd, J=2.9 Hz, J=0.8 Hz, thiophene H$_2$), 7.53 (1H, dd, J=5.0 Hz, J=0.71 Hz, thiophene H$_4$), 7.31 (1H, dd, J=5.06 Hz, J=3.07 Hz, thiophene H$_5$), 4.24 (4H, m, CO$_2$CH$_2$CH$_3$, CO$_2$CH$_2$—), 3.03 (1H, d, J=5.91 Hz, 1H of oxirane), 2.78 (1H, d, J=5.87 Hz, 1H of oxirane), 2.11 (1H, m, aliphatic H), 1.70 (3H, m, aliphatic H), 1.45 (6H, m, aliphatic H), 1.29 (3H, t, J=7.14 Hz, CO$_2$CH$_2$CH$_3$)

$^{13}$C NMR (75 MHz, CDCl$_3$) δ 170.41, 162.87, 133.90, 132.52, 127.90, 125.95, 64.67, 61.60, 56.98, 51.86, 31.16, 29.15, 28.58, 25.82, 24.68, 14.12

EXAMPLE 9

Ethyl-2-[6-(3-thiopheneacetyl)hexyl]-oxirane-2-carboxylic acid

The procedures described in Example 1-1)~1-10) were repeated but using 3-thiopheneacetylic acid instead of 4-chlorobenzoylcarboxylic acid of Example 1-10) to obtain the title compound.

$^1$H NMR (300 MHz, CDCl$_3$) δ 7.29 (1H, dd, J=4.87 Hz, J=3.02 Hz, thiophene H$_5$), 7.15 (1H, m, thiophene H$_2$), 7.04 (1H, dd, J=4.87 Hz, J=0.71 Hz, thiophene H$_4$), 4.23 (2H, m, CO$_2$CH$_2$CH$_3$), 4.09 (2H, t, J=6.64 Hz, CO$_2$CH$_2$—), 3.65 (2H, s, Ar—CH$_2$CO$_2$—), 3.03 (1H, d, J=5.87 Hz, 1H of oxirane), 2.78 (1H, d, J=5.87 Hz, 1H of oxirane), 2.09 (1H, m, aliphatic H), 1.68~1.27 (9H, m, aliphatic H), 1.29 (3H, t, J=7.15 Hz, CO$_2$CH$_2$CH$_3$)

$^{13}$C NMR (75 MHz, CDCl$_3$) δ 171.20, 170.39, 133.70, 128.46, 125.66, 122.77, 64.89, 61.59, 56.96, 51.84, 35.92, 31.11, 29.05, 28.38, 25.63, 24.62, 14.11

EXAMPLE 10

Ethyl-2-[6-(5-nitro-2-furancarboxyl)hexyl]-oxirane-2-carboxylic acid

The procedures described in Example 1-1)~1-10) were repeated but using 5-nitro-2-furancarboxylic acid instead of 4-chlorobenzoylcarboxylic acid of Example 1-10) to obtain the title compound.

$^1$H NMR (300 MHz, CDCl$_3$) δ 7.36 (1H, d, J=3.65 Hz, furan H), 7.39 (1H, d, J=3.69 Hz, furan H), 4.37 (2H, t, J=6.52 Hz, CO$_2$CH$_2$—), 4.22 (2H, m, CO$_2$CH$_2$CH$_3$), 3.04 (1H, d, J=5.76 Hz, 1H of oxirane), 2.79 (1H, d, J=5.77 Hz, 1H of oxirane), 2.11 (1H, m, aliphatic H), 1.67 (3H, m, aliphatic H), 1.43 (6H, m, aliphatic H), 1.29 (3H, t, J=7.06 Hz, CO$_2$CH$_2$CH$_3$)

$^{13}$C NMR (75 MHz, CDCl$_3$) δ 170.34 (2 C's), 157.02, 144.98, 118.66, 111.48, 66.26, 61.57, 56.90, 51.81, 31.07, 28.98, 28.29, 25.56, 24.58, 14.07

EXAMPLE 11

Ethyl-2-[6-(2-thiophenemethoxy)hexyl]oxirane-2-carboxylic acid

1) Dissolved was 1,6-hexanediol (5 g, 42.31 mmol) in dryl tetrahydrofuran (70 ml), and methanesulfonyl chloride (7.2 ml, 93.08 mmol, 2.2 eq.) and triethylamine (14.74 ml, 105.78 mmol, 2.5 eq.) were injected thereto at 0° C. After stirring at 0° C. for about 1.5 hours, the reaction mixture was diluted by adding dichloromethane (250 ml), and the solution washed with distilled water (200 ml×2), 1N aqueous hydrochloric acid (200 ml×2), 5% aqueous sodium bicarbonate solution (200 ml×2) and saturated brine (100 ml). The solution was then dried over anhydrous magnesium sulfate, filtered and concentrated under reduced pressure. The residue was recrystallized from ethyl acetate/n-hexane to give 1,6-hexylmesylate (10.67 g, 91.9%) as white needle crystal.

$^1$H-NMR (300 MHz, CDCl$_3$) δ 4.24(t, 4H), 3.02(s, 6H), 1.8(m, 4H), 1.5(m, 4H)

2) Dissolved was 2-thiophenemethanol (2.0 g, 17.52 mmol) in tetrahydrofuran (100 ml), and sodium hydride (95%) (442 mg, 17.52 mmol, 1.0 eq.) was added thereto at 0° C. After stirring the mixture at the same temperature for 10 minutes, 1,6-dimethanesulfoxyhexane (5.77 g, 21.02 mmol, 1.2 eq.) was added thereto, and the resultant mixture stirred for 16 hours. The reaction mixture was concentrated under reduced pressure to remove tetrahydrofuran, and the residue was diluted with ethyl acetate (200 ml). The solution was washed with distilled water (180 ml), 1N aqueous hydrochloric acid (180 ml×2), 5% sodium bicarbonate (180 ml×2) and saturated brine (100 ml), and then dried over anhydrous magnesium sulfate, filtered and concentrated under reduced pressure. The residue was purified on a column chromatography (ethyl acetate/n-hexane=1/5) to give 6-methanesulfoxy-1-(2-thiophenemethoxy)hexane (3.24 g, 63.2%) as pale yellow oil.

$^1$H-NMR (300 MHz, CDCl$_3$) δ 7.28(q, 1H), 7.0–6.95(m, 2H), 4.66(sd, 2H), 4.22(t, 2H), 3.48(t, 2H), 2.99 (s, 3H), 1.75(m, 2H), 1.6(m, 2H), 1.4(m, 4H)

3) Diethyl malonate (1.85 ml, 12.19 mmol, 1.1 eq.) was dissolved in dry tetrahydrofuran (25 ml), and the solution chilled to 0° C. Sodium hydride (95%) (308 mg, 12.19 mmol, 1.1 eq.) was added thereto, and the resultant mixture stirred about 10 minutes at the same temperature. To the mixture, a solution of 6-methanesulfoxy-1-(2-thiophenemethoxy)hexane (3.24 g, 11.08 mmol) in tetrahydrofuran (20 ml) was slowly added dropwise, and the mixture stirred for a while. After heating under reflux for 16 hours, the mixture was concentrated under reduced pressure to remove tetrahydrofuran. The residue was diluted with ethyl acetate (150 ml) and the solution washed with distilled water (120 ml), 1N aqueous hydrochloric acid (120 ml×2), 5% sodium bicarbonate (120 ml×2) and saturated brine (80 ml). Then the solution was dried over anhydrous magnesium sulfate, filtered, and concentrated under reduced pressure. The obtained residue was purified on a column chromatography (ethyl acetate/n-hexane=1/5) to give diethyl 6-(2-thiophenemethoxy)hexylmalonate (3.5 g, 88.6%) as pale yellow clear oil.

$^1$H-NMR (300 MHz, CDCl$_3$) δ 7.28(q, 1H), 7.0–6.95(m, 2H), 4.65(s, 2H), 4.2(q, 4H), 3.46(t, 2H), 3.3(t, 1H), 1.9(m, 2H), 1.6(m, 2H), 1.32(m, 6H), 1.27(t, 6H)

4) Diethyl 6-(2-thiophenemethoxy)hexylmalonate (3.5 g, 9.82 ml) was dissolved in absolute ethanol (30 ml), and potassium hydroxide (85%) (694 mg, 10.51 mmol, 1.07 eq.) was added thereto. After stirring about 4–5 hours at ambient temperature, the reaction mixture was concentrated under reduced pressure to remove ethanol. The residue was diluted with distilled water (150 ml), and the organic impurities were washed by using ethyl acetate. The water layer was acidified with 1N aqueous hydrochloric acid to pH 2–3, extracted with ethyl acetate (50 ml×3), and washed with 1N aqueous hydrochloric acid (100 ml) and saturated brine (80 ml). The extract was dried over anhydrous magnesium sulfate, filtered and concentrated under reduced pressure to give ethyl 6-(2-thiophenemethoxy)hexyl malonate (2.42 g, 75%) as pale yellow clear oil.

$^1$H-NMR (300 MHz, CDCl$_3$) δ 7.28(q, 1H), 7.0–6.95(m, 2H), 4.66(sd, 2H), 4.22(q, 2H), 3.46(t, 2H), 3.36(t, 1H), 1.9(m, 2H), 1.6(m, 2H), 1.34(m, 6H), 1.28(t, 3H)

5) Dissolved was ethyl 6-(2-thiophenemethoxy) hexylmalonate (2.42 g, 7.37 ml) in dry tetrahydrofuran (70 ml), and sodium hydride (335 mg, 13.27 mmol, 1.8 eq.) was added thereto at 0° C. The mixture was stirred at room temperature for 20 to 30 minutes. When sodium hydride was practically dissolved, Eschenmoser salt (1.64 g, 8.84 mmol, 1.2 eq.) was added in solid state. After stirring for a while, the mixture was heated under reflux for 16 hours. The reaction mixture was concentrated under reduced pressure to remove tetrahydrofuran, and the residue was diluted with ethyl acetate (150 ml), and washed with distilled water (120 ml), 1N aqueous hydrochloric acid (120 ml×2), 5% sodium bicarbonate (120 ml×2) and saturated brine (80 ml). The solution was dried over anhydrous magnesium sulfate, filtered and concentrated under reduced pressure. The residue was purified on a column chromatography (ethyl acetate/n-hexane=1/10) to obtain ethyl 2-[6-(2-thiophenemethoxy)hexyl-2-enepropionate] (1.82 g, 83%) as pale yellow clear oil.

$^1$H-NMR (300 MHz, CDCl$_3$) δ 7.28(q, 1H), 7.0–6.95(m, 2H), 6.12(d, 1H), 5.50(d, 1H), 4.65(sd, 2H), 4.20(q, 2H), 3.47(t, 2H), 2.29(m, 2H), 1.60(m, 2H), 1.45(m, 2H), 1.35(m, 4H), 1.30(t, 3H)

6) To a mixture of distilled water (32 ml), NMO (60 wt %) (1.17 ml, 6.75 mmol, 1.1 eq.) and acetone (28 ml), a solution of 2.5% osmium tetroxide in t-butanol (0.1 M) (3.07 ml, 0.307 mmol, 0.05 eq.), and t-butanol (10 ml) were added and the mixture stirred. The mixture was added to ethyl 2-[6-(2-thiophenemethoxy)hexyl-2-enepropionate (1.82 g, 6.14 mmol), and the resultant mixture stirred at room temperature for 1.5 hours. To the mixture, Na$_2$S$_2$O$_4$ (about 2 g) was added to quench the reaction, and the reaction mixture was concentrated under reduced pressure to remove acetone. The residue was diluted with ethyl acetate (150 ml), and the solution washed with distilled water (120 ml×3) and saturated brine (80 ml), and then dried over anhydrous magnesium sulfate. The residue after filtering and concentrating the solution under reduced pressure was purified on a column chromatography (eluent:ethyl acetate/n-hexane=1/2) to quantitatively obtain ethyl 2,3-dihydroxy-2-[6-(2-thiophenemethoxy)hexylpropionate (2.02 g) as colorless clear oil.

$^1$H-NMR (300 MHz, CDCl$_3$) δ 7.28(q, 1H), 7.0–6.95(m, 2H), 4.65(s, 2H), 4.27(dq-dq, 2H), 3.78(t, 1H), 3.58(dd, 1H), 3.55(s, 1H), 3.46(t, 2H), 2.19(dd, 1H), 1.7–1.5(m, 3H), 1.4–1.0(m, 5H, t, 3H) 7) Ethyl 2,3-dihydroxy-2-[6-(2-thiophenemethoxy)hexylpropionate (2.02 g, 6.11 mmol) was properly dissolved in pyridine (30 ml), and p-toluenesulfonyl chloride (11.65 g, 61.1 mmol, 10 eq.) was added thereto. After stirring about 3 hours, the reaction mixture was diluted by adding ethyl acetate (150 ml). The solution was washed with 1N aqueous hydrochloric acid (120 ml×3), 5% sodium bicarbonate (120 ml×2), distilled water (120 ml) and saturated brine (80 ml), and then dried over anhydrous magnesium sulfate, filtered and concentrated under reduced pressure. The residue was purified on a column chromatography (eluent:ethyl acetate/n-hexane=1/5) to give ethyl 2-hydroxy-3-[4-methoxybenzenesulfoxy)-2-[6-(2-thiophenemethoxy)hexyl]propionate (2.56 g, 86.5%) as white solid.

$^1$H-NMR (300 MHz, CDCl$_3$) δ 7.77(d, 2H), 7.34(d, 2H), 7.28(s, 1H), 6.97(s, br, 2H), 4.63,(s, 2H), 4.22(m, 3H), 3.08(d, 1H), 3.43(t, 2H), 3.35(s, 1H), 2.45(s, 3H), 1.7–1.4 (m, 4H), 1.4–1.15(m, 5H, t, 3H), 1.1(m, 1H)

8) The compound obtained above (2.56 g, 5.28 mmol) was dissolved in absolute ethanol (100 ml), and potassium carbonate (7.3 g, 52.8 mmol, 10 eq.) was added thereto. After stirring at room temperature for 6 hours, the reaction mixture was filtered to remove excess potassium carbonate, and the filtrate concentrated under reduced pressure to remove ethanol. The residue was diluted with ethyl acetate (150 ml), and the solution washed with distilled water (120 ml×2), 5% aqueous citric acid (120 ml×2) and saturated brine (100 ml), and dried over anhydrous magnesium sulfate, filtered and concentrated under reduced pressure. The residue was purified on a column chromatography (eluent:ethyl acetate/n-hexane=1/5) to give ethyl-2-[6-(2- thiophenemethoxy)hexyl]oxirane-2-carboxylic acid (1.41 g, 85.5%) as colorless clear oil.

$^1$H-NMR (300 MHz, CDCl$_3$) δ 7.28(q, 1H), 7.0–6.95(m, 2H), 4.65(s, 2H), 4.22(dq-dq, 2H), 3.46(t, 2H), 3.02(d, 1H), 2.78(d, 1H), 2.08(m, 1H), 1.6(m, 3H), 1.5–1.3(m, 6H), 1.29(t, 3H)

$^{13}$C-NMR (75 MHz, CDCl$_3$) δ 170.45, 141.45, 126.58, 126.15, 125.63, 70.0, 67.31, 61.59, 57.04, 51.84, 31.17, 29.50, 29.32, 25.93, 24.72, 14.13

EXAMPLE 12

Ethyl-2-[6-(3,5-dimethylpyrazole)hexyl]oxirane-2-carboxylic acid

In a 100 ml round-bottomed flask, 60% sodium hydride (158.4 mg, 3.96 mmol) was placed, and the air inside the flask was substituted by argon gas. Dry tetrahydrofuran (5 ml) was added dropwise thereto to form a suspension. After chilling the mixture to 0° C., a solution of 3,5-dimethylpyrazole-1-methanol (500 mg, 3.96 mmol) in dry tetrahydrofuran (3 ml) was added dropwise, and then 1,6-dibromohexane (0.55 ml, 3.6 mmol) was slowly added dropwise thereto. After heating under reflux for 16 hours, the reaction mixture was concentrated under reduced pressure, and the residue was diluted with a mixture of ethyl acetate (150 ml) and water (10 ml). After washing with water (5 ml×2) and saturated brine (5 ml×2), the solution was dried over anhydrous magnesium sulfate, filtered and concentrated under reduced pressure. The residue was purified on a column chromatography (eluent:ethyl acetate/n-hexane= 1/3) to give 340 mg of 6-(3,5-dimethylpyrazole)-1-bromohexanol as colorless oil (yield: 33%).

Mass(EI) 260(M+)

$^1$H NMR (80M, CDCl$_3$) δ 5.80(s, 1H), 3.98(t, 2H), 3.38(t, 2H), 2.25(s, 6H), 1.92–1.42(m, 8H)

After this, the procedures described in Example 11 were repeated to give the final product, ethyl-2-[6-(3,5-dimethyl-pyrazol)hexyl]oxirane-2-carboxylic acid in a high yield.

EXAMPLE 13

Ethyl-2-[6-(5-methoxy-2-thiophenemethoxy)hexyl] oxirane-2-carboxylic acid

The procedures described in Example 11-1)~11-8) were repeated but using 5-methoxy-2-thiophenemethanol instead of 2-thiophenemethanol of Example 11-2) to obtain the title compound.

$^1$H NMR (300 MHz, CDCl$_3$) 6.6(d, 1H), 6.03(d, 1H), 4.48(s, 2H), 4.21(dq-dq,2H), 3.87(s, 3H), 3.42(t, 2H), 3.02 (d, 1H), 2.77(d, 1H), 2.07(m, 1), 1.7–1.5(m, 3H), 1.5–1.3(m, 6H), 1.29(t, 3H)

$^{13}$C NMR (75 MHz, CDCl$_3$) δ 170.4, 166.68, 127.40, 124.09, 102.83, 69.54, 68.01, 61.52, 60.15, 56.99, 51.77, 31.14, 29.46, 29.29, 25.91, 24.68, 14.08

EXAMPLE 14

Ethyl-2-[6-(5-methyl-2-thiophenemethoxy)hexyl] oxirane-2-carboxylic acid

The procedures described in Example 11-1)~11-8) were repeated but using 5-methyl-2-thiophenemethanol instead of 2-thiophenemethanol of Example 11-2) to obtain the title compound.

$^1$H NMR (300MHZ, CDCl$_3$) δ 6.76(d, 1H), 6.60(m,1H), 4.56(s, 2H), 4.22(dq-dq,2H), 3.44(t, 2H), 3.02(d, 1H), 2.78 (d, 1H), 2.46(sd, 3H), 2.08(m,1H),1.7–1.5(m, 3H), 1.5–1.3 (m, 6H), 1.29(t, 3H)

EXAMPLE 15

Ethyl-2-[6-(5-methyl-2-furanmethoxy)hexyl] oxirane-2-carboxylic acid

The procedures described in Example 11-1)~11-8) were repeated but using 5-methyl-2-furanmethanol instead of 2-thiophenemethanol of Example 11-2) to obtain the title compound.

$^1$H NMR(300 MHz, CDCl$_3$) δ 6.17(d, 1H), 5.90(d, 1H), 4.36(s, 2H), 4.21(dq-dq, 2H), 3.44(t, 2H), 3.02(d, 1H), 2.77(d, 1H), 2.28(s, 3H), 2.07(m, 1H), 1.6(m,3H), 1.5–1.3 (m, 6H), 1.29(t, 3H)

$^{13}$C NMR (75 MHz, CDCl$_3$) δ 170.28, 152.31, 150.01, 109.90, 105.98, 69.93, 65.92, 64.68,61.41, 56.87, 51.67, 31.03, 29.32, 29.18, 25.77, 24.58, 15.11, 13.98, 13.50

EXAMPLE 16

Ethyl-2-[6-(2-thiophenethoxy)hexyl]oxirane-2-carboxylic acid

The procedures described in Example 11-1)~11-8) were repeated but using 2-thiophenethanol instead of 2-thiophenemethanol of Example 11- 2) to obtain the title compound.

$^1$H NMR (300 MHz, CDCl$_3$) δ 7.13(dd, 1H), 6.92(dd, 1H), 6.84(dd, 1H), 4.21(dq-dq, 2H), 3.64(t, 2H), 3.44(t, 2H), 3.08(t, 2H), 3.02(d, 1H), 2.77(d,1H), 2.08(m, 1H), 1.7–1.3 (m, 9H), 1.29(t, 3H)

$^{13}$C NMR (75 MHz, CDCl$_3$) δ 170.31, 141.29, 126.49, 124.90, 123.46, 71.25, 70.83, 61.45, 56.91, 51.71, 31.05, 30.36, 29.42, 29.21, 25.84, 24.62, 14.01

EXAMPLE 17

Ethyl-2-[6-(5-chloro-2-thiophenemethoxy)hexyl] oxirane-2-carboxylic acid

The procedures described in Example 11-1)~11-8) were repeated but using 5-chloro-2-thiophenemethanol instead of 2-thiophenemethanol of Example 11-2) to obtain the title compound.

$^1$H NMR (300 MHz, CDCl$_3$) δ 6.77(d, 1H), 6.74(d, 1H), 4.54(s, 2H), 4.22(dq-dq,2H), 3.45(t,2H), 3.02(d, 1H), 2.77 (d, 1H), 2.08(m, 1H), 1.7–1.5(m, 3H),1.5–1.3(m, 6H), 1.29 (t, 3H)

$^{13}$C NMR (75 MHz, CDCl$_3$) δ 170.40, 140.48, 129.91, 125.52, 125.27, 70.07, 67.53, 6 51.54,56.99, 51.79, 31.14, 29.44, 29.27, 25.88, 24.68, 14.10

EXAMPLE 18

Ethyl-2-[6-(3-chloro-2-thiophenemethoxy)hexyl] oxirane-2-carboxylic acid

The procedures described in Example 11-1)~11-8) were repeated but using 3-chloro-2-thiophenemethanol instead of 2-thiophenemethanol of Example 11-2) to obtain the title compound.

$^1$H NMR (300 MHz, CDCl$_3$) δ 7.26(d, 1H), 6.89(d, 1H), 4.63(s, 2H), 4.22(dq-dq,2H), 3.49(t, 2H), 3.02(d, 1H), 2.77 (d, 1H), 2.08(m, 1H), 1.6(m, 3H), 1.5–1.4(m, 6H), 1.29(t, 3H)

$^{13}$C NMR (75 MHz, CDCl$_3$) δ 170.39, 134.10, 127.46, 124.67, 123.41, 70.34, 64.80, 61.53, 56.99, 51.77, 31.14, 29.41, 29.25, 25.85, 24.68, 14.09

EXAMPLE 19

Ethyl-2-[6-(4-methoxy-2-thiophenemethoxy)hexyl]oxirane-2-carboxylic acid

The procedures described in Example 11-1)~11-8) were repeated but using 4-methoxy-2-thiophenemethanol instead of 2-thiophenemethanol of Example 11-2) to obtain the title compound.

$^1$H NMR (300 MHz, CDCl$_3$) δ 6.65 (1H, s, thiophene H), 6.17 (1H, s, thiophene H), 4.54 (2H, s, Ar—CH$_2$O—), 4.22 (2H, m, CO$_2$CH$_2$CH$_3$), 3.78 (3H, s, —OCH$_3$), 3.45 (2H, t, J=6.43 Hz, ArCH$_2$O—CH$_2$—), 3.02 (1H, d, J=5.84 Hz, 1H of oxirane), 2.77 (1H, d, J=5.83 Hz, 1H of oxirane), 2.07 (1H, m, aliphatic H), 1.7~1.57 (3H, m, aliphatic H), 1.44~1.31 (6H, m, aliphatic H), 1.29 (3H, t, J=7.13 Hz, CO$_2$CH$_2$CH$_3$)

$^{13}$C NMR (75 MHz, CDCl$_3$) δ 170.37, 157.54, 140.54, 118.25, 96.45, 70.03, 67.63, 61.50, 57.09, 56.97, 51.74, 31.11, 29.43, 29.26, 25.85, 24.66, 14.06

EXAMPLE 20

Ethyl-2-[6-(3-thiophenemethoxy)hexyl]oxirane-2-carboxylic acid

The procedures described in Example 11-1)~11-8) were repeated but using 3-thiophenemethanol instead of 2-thiophenemethanol of Example 11-2) to obtain the title compound.

$^1$H NMR (300 MHz, CDCl$_3$) δ 7.30 (1H, d, J=4.82 Hz, J=2.97 Hz, thiophene H$_5$), 7.20 (1H, sd, thiophene H$_2$), 7.07 (1H, d(br), J=4.39 Hz, thiophene H$_4$), 4.50 (2H, s, Ar—CH$_2$O—), 4.21 (2H, m, CO$_2$CH$_2$CH$_3$), 3.44 (2H, t, J=6.55 Hz, ArCH$_2$O—CH—). 3.02 (1H, d, J=5.91 Hz, 1H of oxirane), 2.77 (1H, d, J=5.88 Hz, 1H of oxirane), 2.06 (1H, m, aliphatic H), 1.6 (3H, m, aliphatic H), 1.36 (6H, m, aliphatic H), 1.29 (3H, t, J=7. 113 Hz, CO$_2$CH$_2$CH$_3$)

$^{13}$C NMR (75 MHz, CDCl$_3$) δ 170.37, 139.74, 127.24, 125.81, 122.46, 70.19, 68.04, 61.50, 56.96, 51.75, 31.11, 29.51, 29.27, 25.92, 24.66, 14.06

EXAMPLE 21

Ethyl-2-[6-(3-thiophenethoxy)hexyl]oxirane-2-carboxylic acid

The procedures described in Example 11-1)~11-8) were repeated but using 3-thiophenethanol instead of 2-thiophenemethanol of Example 11-2) to obtain the title compound.

$^1$H NMR (300 MHz, CDCl$_3$) δ 7.26 (1H, dd, J=4.89 Hz, J=2.99 Hz, thiophene H$_5$), 7.02 (1H, m, thiophene H$_2$), 6.98 (1H, dd, J=4.9 Hz, J=1.34 Hz, thiophene H$_4$), 4.22 (2H, m, CO$_2$CH$_2$CH$_3$), 3.62 (2H, t, J=7.09 Hz, Ar—CH$_2$CH$_2$O—), 3.43 (2H, t, J=6.59 Hz, ArCH$_2$CH$_2$O—CH$_2$—), 3.03 (1H, d, J=5.87 Hz, 1H of oxirane), 2.91 (2H, t, J=7.16 Hz, Ar—CH$_2$CH$_2$O—), 2.78 (1H, d, J=5.92 Hz, 1H of oxirane), 2.1 (1H, m, aliphatic H), 1.7~1.3 (9H, m, aliphatic H), 1.29 (3H, t, J=7.16 Hz, CO$_2$CH$_2$CH$_3$)

$^{13}$C NMR (75 MHz, CDCl$_3$) δ 170.34, 139.24, 128.39, 125.04, 120.91, 70.86, 70.80, 61.48, 56.93, 51.73, 31.07, 30.6 3, 29.45, 29.23, 25.87, 24.62, 14.02

EXAMPLE 22

Ethyl-2-[6-(2-thiophenoxy)hexyl]oxirane-2-carboxylic acid

The procedures described in Example 11-1)~11-8) were repeated but using 2-thiophenone instead of 2-thiophenemethanol of Example 11-2) to obtain the title compound.

$^1$H NMR (300 MHz, CDCl$_3$) δ 6.71 (1H, dd, J=3.76 Hz, J=5.75 Hz, thiophene H$_4$), 6.53 (1H, dd, J=5.77 Hz, J=1.45 Hz, thiophene H$_5$), 6.19 (1H, dd, J=3.75 Hz, J=1.44 Hz, thiophene H$_3$), 4.20 (2H, m, CO$_2$CH$_2$CH$_3$) 4.02 (2H, t, J=6.44 Hz, ArO—CH$_2$—), 3.03 (1H, d, J=5.86 Hz, 1H of oxirane), 2.78 (1H, d, J=5.91 Hz, 1H of oxirane), 2.11 (1H, m, aliphatic H), 1.77 (3H, m, aliphatic H), 1.45 (6H, m, aliphatic H), 1.29 (3H, t, J=7.13 Hz, CO$_2$CH$_2$CH$_3$)

$^{13}$C NMR (75 MHz, CDCl$_3$) δ 170.39, 165.72, 124.65, 111.67, 104.50, 73.74, 61.58, 56.97, 51.83, 31.12, 29.13, 28.99, 25.65, 24.65, 14.10

Experimental Example 1

Blood Glucose Lowering Effects of the Compounds Prepared by the Procedures of Example 1~6, 11~18

Two groups of male diabetes-induced Sprague-Dawley rats (each of 4–5 rats weighing about 250 g) were used for this experiment. 45 mg/kg of streptozotocin (STZ) dissolved in 0.1M citrate buffer (pH 4.5, 0–4° C.) was injected to the tail vein of fasted rats for 1 day. After elapse of 7 days, their blood glucose concentration were measured and animals having the blood serum concentration of more than 350 mg/dl were used as diabetes-induced rats for this experiment. The rats were intravenously administered at a daily dose of 1 ml/kg, while the normal control group received equal volume of 0.1M citrate buffer.

7 days after being treated with streptozotocin, diabetes-induced rats were orally administered at a dose of 50 mg/kg of the compounds prepared by the procedures of Examples 1–6, 11~18. Then, at time intervals of 90 mins, 120 mins and 180 mins, their blood glucose concentrations were measured and the smallest values were taken. The compounds of Example 1-13 were dissolved in 30% ethanol until its final concentration became 2 ml/kg, while the control group was orally received equal volume of 30% ethanol.

Significant difference between two groups was determined by ANOVA test, together with a post hoc test using Newman-Keuls test.

The test results was shown in the following table 1.

TABLE 1

Blood glucose lowering effects of the Examples 1 ~ 6, 11 ~ 18

| Compound | Blood glucose lowering rate % |
| --- | --- |
| Example 1 | 11.8 |
| Example 2 | 28.2 |
| Example 3 | 8.1 |
| Example 4 | 21.6 |
| Example 5 | 16.8 |
| Example 6 | 24.1 |
| Example 11 | 75.9 |
| Example 12 | 47 |
| Example 13 | 5.9 |
| Example 14 | 33.7 |
| Example 15 | 6.8 |
| Example 16 | 5.6 |
| Example 17 | 19.2 |
| Example 18 | 30.7 |

As noted in the above table 1, the compounds of this invention have proven to have remarkable blood glucose lowering effects on diabetes-induced rats.

Experimental Example 2

Toxicity test

The acute toxicity tests on rats were performed using the compound prepared by the procedure of the Example 1.

Mature rats weighing 200–250 g were orally given the compound of the Example 1 dissolved in ethylacetate in parallel with its gradually increasing concentration. Then $LD_{50}$ was 487.1 mg/kg, which was calculated by number of killed animals.

The test results was shown in the following table 2.

TABLE 2

Result of toxicity test

| dose concentration(mg/kg) | number of killed animals/ number of animals per group. |
| --- | --- |
| 160 | 0/10 |
| 300 | 1/10 |
| 400 | 2/10 |
| 500 | 5/10 |
| 600 | 8/10 |

We claim:

1. A compound of the following formula 1 or a pharmaceutically acceptable salt thereof;

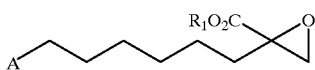

Wherein:

A is one selected from the radicals expressed by the following (i), (ii), (iii) and (iv);

(i)

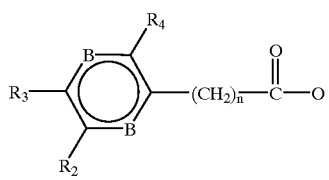

(ii)

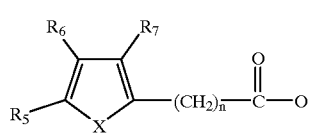

(iii)

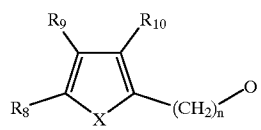

(iv)

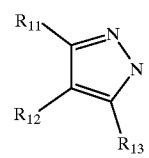

$R_1$ represents a lower alkyl, (wherein, $R_2$~$R_{13}$ represent independently hydrogen, halogen, alkoxy, lower alkyl, hydroxy, alkenyl, alkynyl, cyano or amino group; B is independently nitrogen or carbon; X is oxygen or sulfur; n denotes 0, 1 or 2).

2. A compound of the formula 1 or a pharmaceutically acceptable salt thereof according to claim 1, wherein:

$R_2$ is hydrogen, bromine or chlorine; $R_3$ is hydrogen, methyl, n-butyl, chlorine or methoxy group; $R_4$ is hydrogen or methoxy group.

3. A compound of the formula 1 or a pharmaceutically acceptable salt thereof according to claim 1, wherein:

$R_5$ is hydrogen or bromine; $R_6$ and $R_7$ are hydrogen.

4. A compound of the formula 1 or a pharmaceutically acceptable salt thereof according to claim 1, wherein:

$R_8$ is hydrogen, methyl, chlorine or methoxy group; $R_9$ is hydrogen; $R_{10}$ is hydrogen or chlorine.

5. A compound of the formula 1 or a pharmaceutically acceptable salt thereof according to claim 1, wherein:

$R_{11}$ and $R_{13}$ are methyl; $R_{12}$ is hydrogen.

6. A compound of the formula 1 or a pharmaceutically acceptable salt thereof according to claim 1, wherein $R_1$ is an ethyl group.

7. A compound of the formula 1 or a pharmaceutically acceptable salt thereof according to claim 1, wherein n denotes 0.

8. A compound of the formula 1 or a pharmaceutically acceptable salt thereof according to claim 1, wherein n denotes 1.

9. A process for manufacturing the compound of the chemical formula 1, wherein:

a) 1,6-hexanediol of the structural formula 2, a well known substance and starting material, is treated with sodium hydride as a base to synthesize 6-benzyloxy-1-hexanol of the structural formula 3 with substituted benzyl ring;

b) The compound of the formula 3 is tosylated to furnish the compound of the structural formula 4;

c) The compound of the structural formula 4 is reacted with dimalonate to synthesize dialkyl-6-benzoxihexylmalonate of the general formula 5;

d) The compound of the general formula 5 is hydrolyzed using potassium hydride to furnish the compound of the general formula 6;

e) Eschernmorser's salt is added to the compound of the general formula 6 to synthesize the alpha, beta-unsaturated ester of the general formula 7;

f) The compound of the general formula 7 is catalyzed by osmium tetroxide to give the compound of the general formula 8;

g) The compound of the general formula 8 is further tosylated to synthesize alkyl-2-hydroxy-3-(4-methylbenzenesulfoxy)-2-(6-benzoxy)hexylpropionic acid of the general formula 9;

h) The compound of the general formula 9 is treated with potassium carbonate as a base to give alkyl-2-(6-benzoxy)hexyloxiran-2-carboxylic acid of the general formula 10, followed by the intermolecular cyclic reaction;

i) The compound of the general formula 10 is hydrogenated to give the compound of the general formula 11 with thereof benzyl group deprotected;

j) The compound of the general formula 11 is treated with DCC, DMAP and methane dichloride and give oxirane carboxylic acid derivative of the formula 1, a desired compound, via esterification, etherification or amidofication with AH of the general formula;

(wherein: A is the same as defined above)

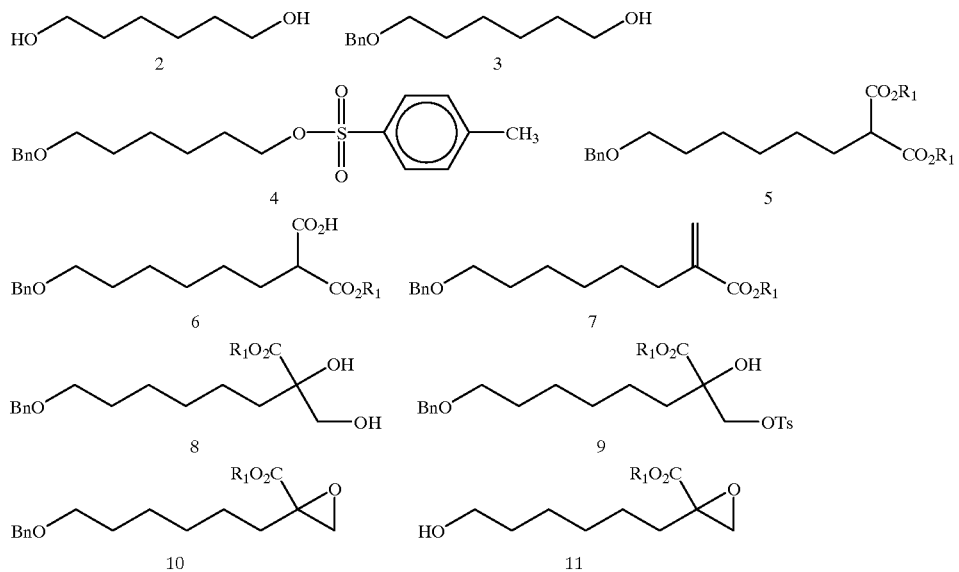
10. An antidiabetic agent containing the compound or a pharmaceutically thereof expressed by the formula 1 according to claim 1.
* * * * *

UNITED STATES PATENT AND TRADEMARK OFFICE
CERTIFICATE OF CORRECTION

PATENT NO. : 6,013,666
DATED : January 117, 2000
INVENTOR(S) : Sang Sup JEW et al.

It is certified that error appears in the above-identified patent and that said Letters Patent is hereby corrected as shown below:

Claim 9, column 20, lines 29-30, delete ", a well known substance and starting material,".

Signed and Sealed this

Twenty-ninth Day of May, 2001

Attest:

NICHOLAS P. GODICI

*Attesting Officer*    *Acting Director of the United States Patent and Trademark Office*

UNITED STATES PATENT AND TRADEMARK OFFICE
CERTIFICATE OF CORRECTION

PATENT NO. : 6,013,666
DATED : August 15, 2000
INVENTOR(S) : Fernando del Corral, Percy Jaquess, and David Oppong It is certified that error appears in the above-identified patent and that said Letters Patent is hereby corrected as shown below:

Column 12, claim 4,
Line 59, "B' is {-[$CH_2$—CH(OH) —$CH_2$—$N^+R'_2$ '3($CHR'$)$_n$-NH—" should read -- B' is {-[$CH_2$—CH(OH) —$CH_2$—$N^+R_2$—($CHR'$)$_n$-NH— --.

Column 13, claim 4,
Line 1, "X" should read -- $X^-$ --.

Column 15, claim 24,
Line 14, "$C_1$-C,0" should read -- $C_1$-$C_{10}$ --.

Column 15, claim 25,
Line 25, in formula III, the line spacing is improper whereas some of the text overlaps, the formula reads as:

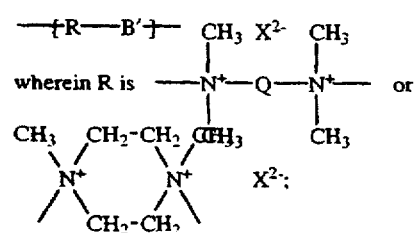

(III)

When formula (III) should read as

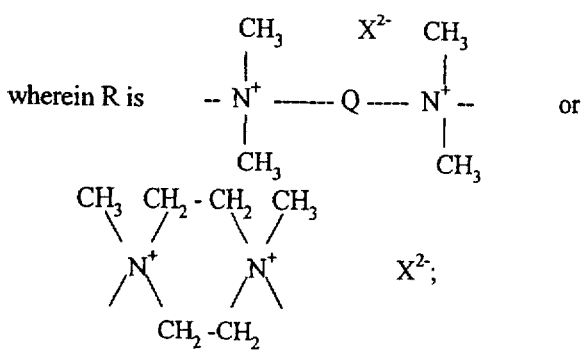

(III)

UNITED STATES PATENT AND TRADEMARK OFFICE
CERTIFICATE OF CORRECTION

PATENT NO. : 6,013,666
DATED : August 15, 2000
INVENTOR(S) : Fernando del Corral, Percy Jaquess, and David Oppong It is certified that error appears in the above-identified patent and that said Letters Patent is hereby corrected as shown below:

Column 16, claim 34,
Line 18, "26" should read -- 20 --.

Column 16, claim 37,
Line 45, "$C_2$-$C_{100}$" should read -- $C_2$-$C_{10}$ --.

Column 17, claim 37,
Line 5, "$R^2$-" should read -- R' --

Signed and Sealed this

Twenty-fifth Day of December, 2001

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,013,666
DATED : August 15, 2000
INVENTOR(S) : Fernando Del Corral, Percy Jaquess, and David Oppong It is certified that error appears in the above-identified patent and that said Letters Patent is hereby corrected as shown below:

Column 12, claim 4,
Line 59, "B' is {-[CH$_2$–CH(OH) –CH$_2$–N$^+$R'$_2$– '3(CHR')$_n$-NH–" should read
-- B' is {-[CH$_2$–CH(OH) –CH$_2$–N$^+$R'$_2$–(CHR')$_n$-NH– --.

Column 13, claim 4,
Line 1, "X" should read -- X$^-$ --.

Column 15, claim 24,
Line 14, "C$_1$-C,0" should read -- C$_1$-C$_{10}$ --.

Column 15, claim 25,
Line 25, in formula III, the line spacing is improper whereas some of the text overlaps, the formula reads as:

(III)

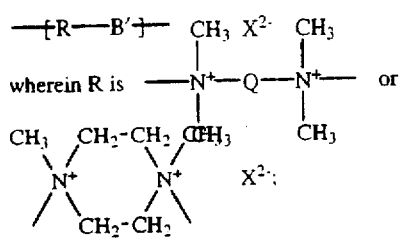

UNITED STATES PATENT AND TRADEMARK OFFICE
CERTIFICATE OF CORRECTION

PATENT NO. : 6,013,666
DATED : August 15, 2000
INVENTOR(S) : Fernando Del Corral, Percy Jaquess, and David Oppong It is certified that error appears in the above-identified patent and that said Letters Patent is hereby corrected as shown below:

When formula (III) should read as $$--------[-R--------B'-]-------- \qquad (III)$$

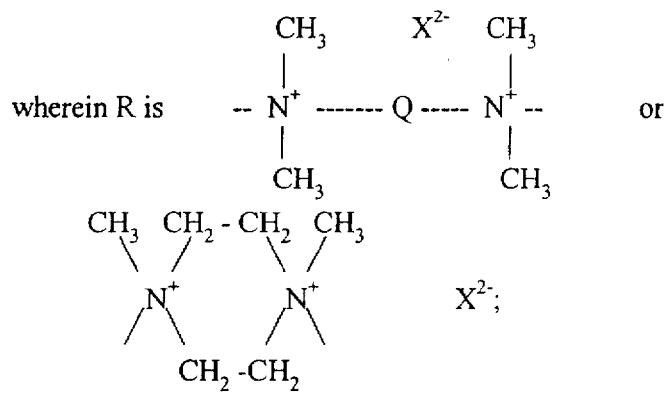

UNITED STATES PATENT AND TRADEMARK OFFICE
CERTIFICATE OF CORRECTION

PATENT NO. : 6,013,666
DATED : August 15, 2000
INVENTOR(S) : Fernando Del Corral, Percy Jaquess, and David Oppong It is certified that error appears in the above-identified patent and that said Letters Patent is hereby corrected as shown below:

Column 16, claim 34,
Line 18, "26" should read -- 20 --.

Column 16, claim 37,
Line 45, "$C_2$-$C_{100}$" should read -- $C_2$-$C_{10}$ --.

Column 17, claim 37,
Line 5, "$R^{2\text{-}}$" should read -- R` --.

Signed and Sealed this

Twelfth Day of February, 2002

Attest:

JAMES E. ROGAN

UNITED STATES PATENT AND TRADEMARK OFFICE
CERTIFICATE OF CORRECTION

PATENT NO.      : 6,013,666
DATED           : January 11, 2000
INVENTOR(S)     : Sang Sup Jew et al.

It is certified that error appears in the above-identified patent and that said Letters Patent is hereby corrected as shown below:

This certificate supersedes certificate of correction issued February 12, 2002, the number was erroneously mentioned and should be deleted since no certificate of correction was granted.

Signed and Sealed this

Fifth Day of March, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.   : 6,013,666
DATED        : January 11, 2000
INVENTOR(S)  : Sang Sup Jew et al.

It is certified that error appears in the above-identified patent and that said Letters Patent is hereby corrected as shown below:

This certificate supersedes Certificate of Correction issued December 25, 2001, the number was erroneously mentioned and should be deleted since no Certificate of Correction was granted.

Signed and Sealed this

Twelfth Day of November, 2002

*Attest:*

*Attesting Officer*

JAMES E. ROGAN
*Director of the United States Patent and Trademark Office*